US012631606B2

(12) United States Patent
Amini et al.

(10) Patent No.: US 12,631,606 B2
(45) Date of Patent: May 19, 2026

(54) RADAR-ASSISTED ENVIRONMENT MONITORING

(71) Applicant: Cisco Technology, Inc., San Jose, CA (US)

(72) Inventors: Peiman Amini, Fremont, CA (US); Vishal S. Desai, San Jose, CA (US); Ardalan Alizadeh, Milpitas, CA (US)

(73) Assignee: Cisco Technology, Inc., San Jose, CA (US)

( * ) Notice: Subject to any disclaimer, the term of this patent is extended or adjusted under 35 U.S.C. 154(b) by 347 days.

(21) Appl. No.: 18/061,966

(22) Filed: Dec. 5, 2022

(65) Prior Publication Data
US 2024/0183830 A1      Jun. 6, 2024

(51) Int. Cl.
| | |
|---|---|
| *G01N 33/00* | (2006.01) |
| *G01S 13/04* | (2006.01) |
| *H04W 88/08* | (2009.01) |

(52) U.S. Cl.
CPC .......... *G01N 33/0006* (2013.01); *G01S 13/04* (2013.01); *H04W 88/08* (2013.01)

(58) Field of Classification Search
CPC ... G01N 33/0006; G01S 13/04; G01S 13/886; G01S 7/40; H04W 88/08
See application file for complete search history.

(56) References Cited

U.S. PATENT DOCUMENTS

| | | |
|---|---|---|
| 2016/0100233 A1 | 4/2016 | Fadell et al. |
| 2022/0060856 A1 | 2/2022 | Wellig et al. |

| | | | |
|---|---|---|---|
| 2022/0198162 A1 * | 6/2022 | Eizenberg | ............. G01S 5/0295 |
| 2022/0225063 A1 | 7/2022 | Marschalkowski et al. | |
| 2023/0126832 A1 * | 4/2023 | White | .................... G06Q 10/06 |
| | | | 705/7.13 |
| 2023/0398993 A1 * | 12/2023 | Strauss | .................. B60N 2/002 |

(Continued)

FOREIGN PATENT DOCUMENTS

| | | |
|---|---|---|
| EP | 3739356 A1 | 11/2020 |
| WO | WO-2020141417 A1 * | 7/2020 ............. G01S 13/88 |

(Continued)

OTHER PUBLICATIONS

Cisco, "What is a Smart Building", <https://www.cisco.com/c/en/us/solutions/smart-building/what-is-a-smart-building.html>, accessed Dec. 7, 2022.

(Continued)

*Primary Examiner* — William Kelleher
*Assistant Examiner* — Kenneth W Good
(74) *Attorney, Agent, or Firm* — Patterson + Sheridan, LLP

(57) ABSTRACT

Method and apparatus including a wireless access point system with an environmental sensor adapted to detect an environmental parameter of an area and a wireless access point. The wireless access point includes a wireless communication module adapted to provide a wireless communication signal; a radar module adapted to provide, via the wireless communication signal, a radar with a field of view of or within the area; and an object detection module adapted to determine if one or more sentient beings are present within the field of view, the wireless access point system adapted to calibrate the environmental sensor based on the object detection module determining, for a time duration, an absence of the one or more sentient beings.

17 Claims, 8 Drawing Sheets

(56) References Cited

U.S. PATENT DOCUMENTS

| | | | |
|---|---|---|---|
| 2024/0080666 A1 * | 3/2024 | Balmakhtar | ........ H04W 12/062 |
| 2024/0177491 A1 * | 5/2024 | Ding | ....................... G01S 7/003 |
| 2024/0276469 A1 * | 8/2024 | Thathramveedu | .. H04W 72/566 |

FOREIGN PATENT DOCUMENTS

| | | | | |
|---|---|---|---|---|
| WO | WO-2021043651 A1 * | 3/2021 | .............. | F24F 11/46 |
| WO | WO-2021194944 A1 * | 9/2021 | ........... | A61B 5/1113 |
| WO | 2022124503 A1 | 6/2022 | | |

OTHER PUBLICATIONS

Eitan et al., "Wi-Fi Sending in 60GHZ band", Sep. 16, 2019.
Li et al., "Passive WiFi Radar for Human Sensing Using A Stand-Alone Access Point", IEEE, Jul. 14, 2020.
International Search Report and Written Opinion for International Application No. PCT/US2023/080946, mailed May 14, 2024, 22 Pages.

* cited by examiner

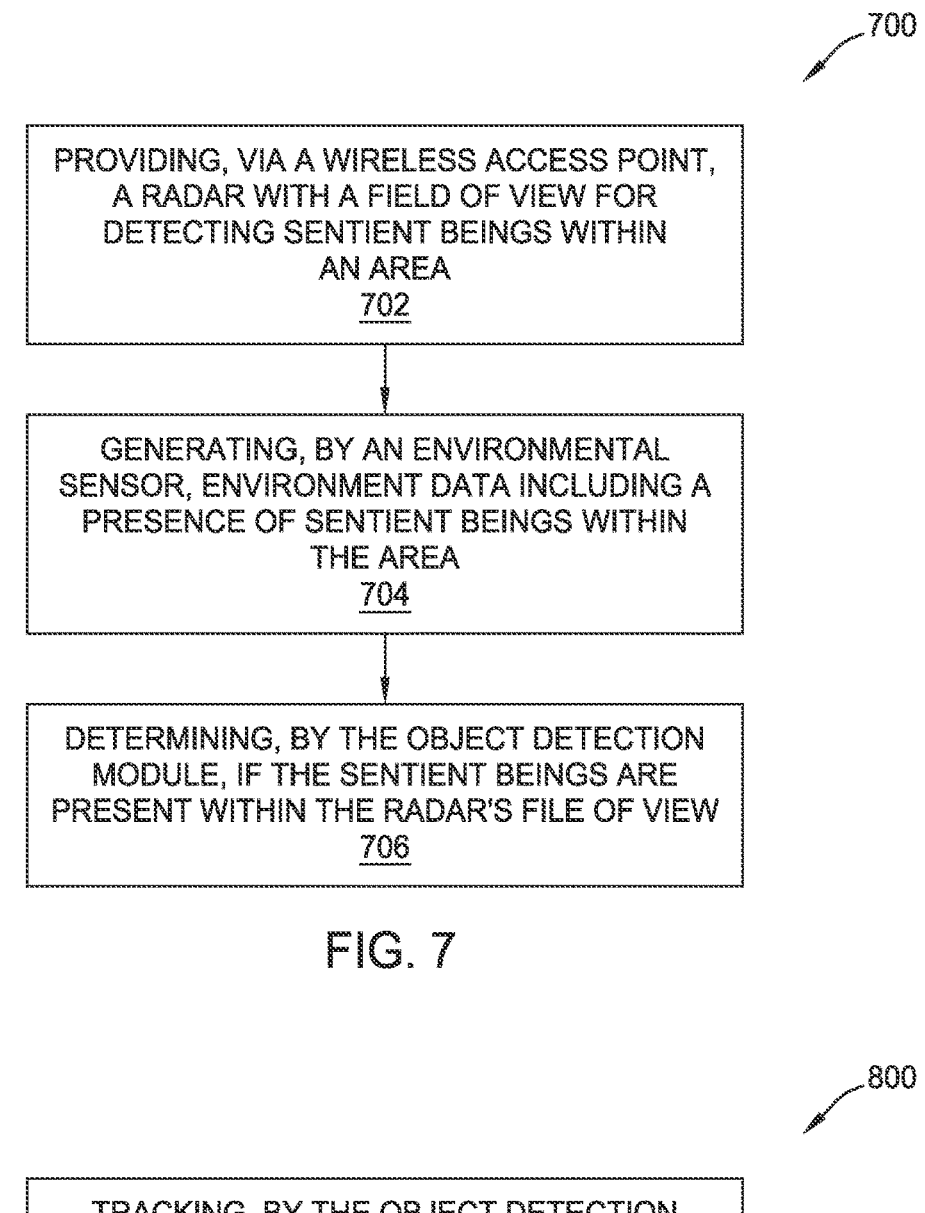

700

PROVIDING, VIA A WIRELESS ACCESS POINT,
A RADAR WITH A FIELD OF VIEW FOR
DETECTING SENTIENT BEINGS WITHIN
AN AREA
702

GENERATING, BY AN ENVIRONMENTAL
SENSOR, ENVIRONMENT DATA INCLUDING A
PRESENCE OF SENTIENT BEINGS WITHIN
THE AREA
704

DETERMINING, BY THE OBJECT DETECTION
MODULE, IF THE SENTIENT BEINGS ARE
PRESENT WITHIN THE RADAR'S FILE OF VIEW
706

TRACKING, BY THE OBJECT DETECTION
MODULE, DETECTED OBJECTS ARRANGED
WITHIN THE FIELD OF VIEW
706a

FILTERING THE DETECTED OBJECTS BASED
ON AT LEAST THE ENVIRONMENT DATA SUCH
THAT THE OBJECT DETECTION MODULE
EXCLUDES NON-SENTIENT DETECTED
OBJECTS
706b

FIG. 8

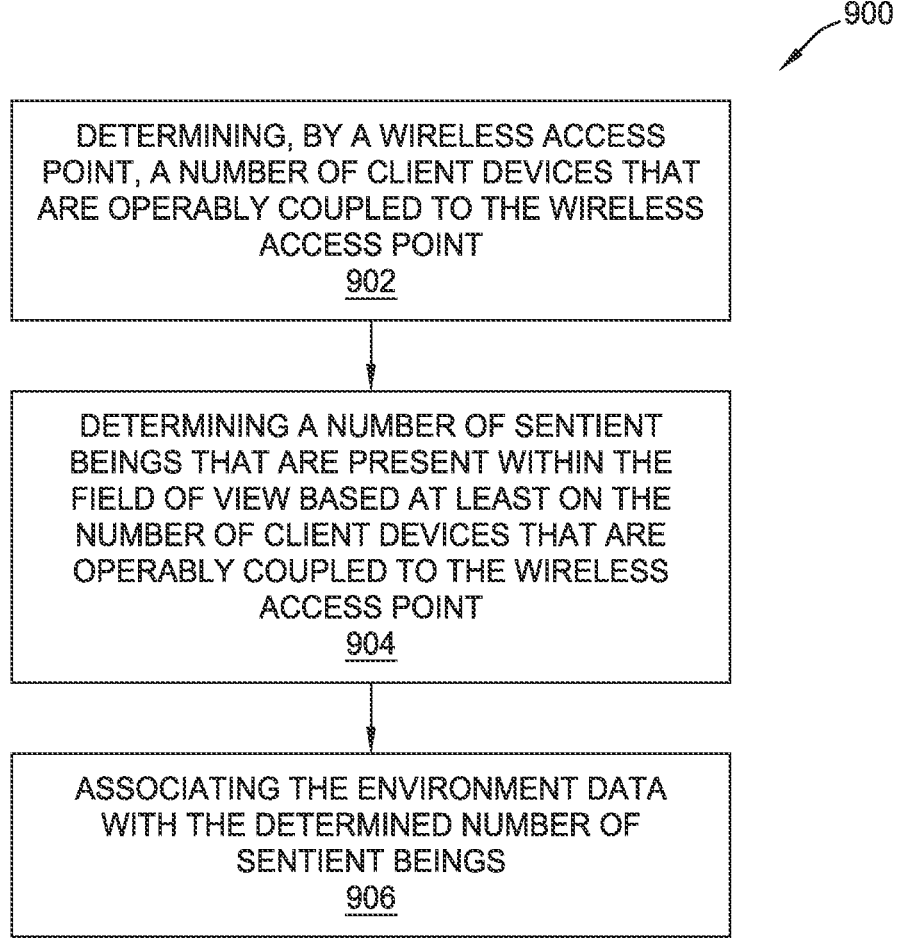

900

DETERMINING, BY A WIRELESS ACCESS
POINT, A NUMBER OF CLIENT DEVICES THAT
ARE OPERABLY COUPLED TO THE WIRELESS
ACCESS POINT
902

DETERMINING A NUMBER OF SENTIENT
BEINGS THAT ARE PRESENT WITHIN THE
FIELD OF VIEW BASED AT LEAST ON THE
NUMBER OF CLIENT DEVICES THAT ARE
OPERABLY COUPLED TO THE WIRELESS
ACCESS POINT
904

ASSOCIATING THE ENVIRONMENT DATA
WITH THE DETERMINED NUMBER OF
SENTIENT BEINGS
906

FIG. 9

RADAR-ASSISTED ENVIRONMENT MONITORING

TECHNICAL FIELD

Embodiments presented in this disclosure generally relate to monitoring environmental parameters. More specifically, embodiments disclosed herein relate to radar-assisted environment monitoring.

BACKGROUND

Tracking and monitoring occupancy levels in office buildings and meeting rooms are important tasks for facility managers. Such managers track occupancy for general planning, optimizing operations, and compliance with occupancy limits. Typically, IR sensors are used for motion and presence detection. These methods may provide a sense of building or room occupancy, but with fundamental limitations. This results in organizations being unable to accurately track occupancy data to improve their spaces and experiences for employees and customers.

More advance devices such as cameras and LiDAR can be used to detect people entering and exiting a space, but are designed for particular, narrow applications, which limits their deployment to specific areas. Cameras and LiDAR may also be costly for measuring large areas by requiring many sensors for effective monitoring.

Carbon dioxide (CO2 or $CO_2$) sensors have several limitations, particularly for monitoring enclosed spaces. For example, rising $CO_2$ level readings may be an indicator of the presence of people, but a $CO_2$ sensors' accuracy may drift over time, particularly for cheaper, compact, and less sophisticated sensors. Such sensors need to be calibrated annually or every few months, thereby introducing uncertainty into the sensor data, especially between re-calibrations.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate typical embodiments and are therefore not to be considered limiting; other equally effective embodiments are contemplated.

FIG. 7 depicts an example of an environment monitoring method.

FIG. 8 depicts an example of an environment monitoring method.

FIG. 9 depicts an example of an environment monitoring method.

To facilitate understanding, identical reference numerals have been used, where possible, to designate identical elements that are common to the figures. It is contemplated that elements disclosed in one embodiment may be beneficially used in other embodiments without specific recitation.

DESCRIPTION OF EXAMPLE EMBODIMENTS

Overview

Figure 1:
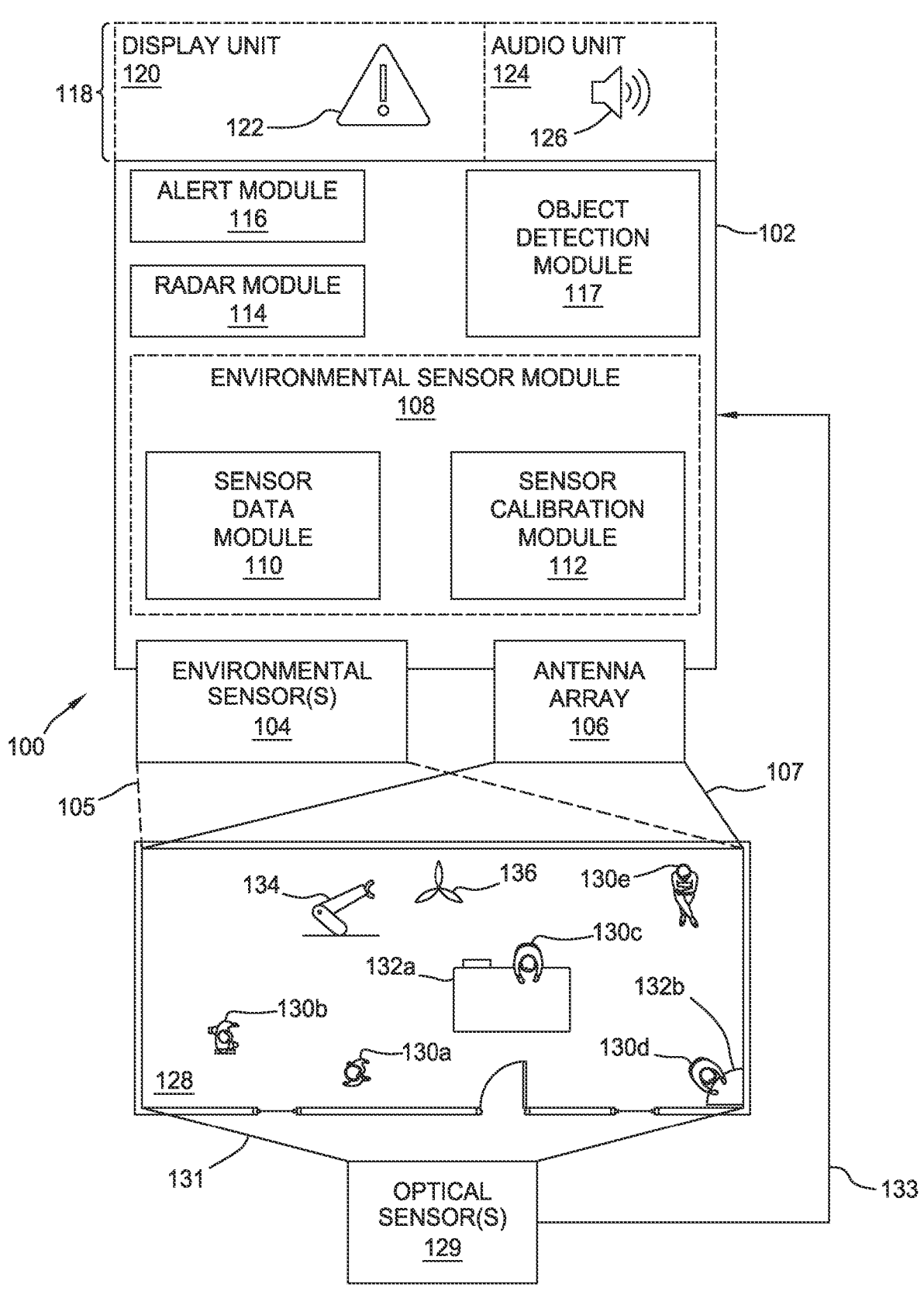
FIG. 1 depicts examples of an environment monitoring system.

In one embodiment presented in this disclosure, a method includes providing a radar using a wireless communication signal of a wireless access point, the radar arranged with a field of view for detecting sentient beings within an area that is monitored by a carbon dioxide sensor; determining, for a time duration, an absence of sentient beings within the field of view of the radar; and calibrating the carbon dioxide sensor to a default value in response to determining the absence of the sentient beings.

In one aspect, in combination with any example method above or below, the wireless access point is operably coupled to the carbon dioxide sensor. In one aspect, in combination with any example method above or below the wireless access point includes the carbon dioxide sensor.

In one aspect, in combination with any example method above or below, the method further includes providing, by the wireless communication signal, a wireless communication channel with a center frequency between 50 GHz and 70 GHz. In one aspect, in combination with any example method above or below, the method further includes providing, by the wireless access point, a plurality of wireless communication channels with respective center frequencies between 1 GHz and 70 GHz.

In one aspect, in combination with any example method above or below, the determining the absence of sentient beings within the field of view of the radar is performed by the wireless access point; and calibrating the carbon dioxide sensor to the default value in response to determining the absence of the sentient beings is performed by the wireless access point.

In one aspect, in combination with any example method above or below, the method further includes determining, based on carbon dioxide sensor data, a floor value as the default value.

In one aspect, in combination with any example method above or below, the method further includes determining a number of sentient beings present within the field of view and associating carbon dioxide sensor data with the number of sentient beings.

In one embodiment presented in this disclosure, a method for operating a radar system, which includes a wireless access point, an object detection module, and an environmental sensor, includes providing, using the wireless access point, a radar with a field of view for detecting sentient beings within an area that is monitored by the environmental sensor; generating, by the environmental sensor, environment data indicating a presence of one or more of the sentient beings within the area; and determining, by the object detection module, if the sentient beings are present within the field of view, the determining step including: tracking, by the object detection module, detected objects arranged within the field of view; and filtering the detected objects based on at least the environment data such that the object detection module excludes non-sentient detected objects.

In one aspect, in combination with any example method above or below, the method further includes determining, by the wireless access point, a number of client devices that are operably coupled to the wireless access point via a wireless communication channel.

In one aspect, in combination with any example method above or below, the determining step by the object detection module includes determining that the one or more of the sentient beings are present within the field of view based at least on the number of client devices that are operably coupled to the wireless access point.

In one aspect, in combination with any example method above or below, the filtering step includes determining, by the object detection module, a baseline cluster arrangement based at least on the environment data, the baseline cluster arrangement indicating an absence of the sentient beings.

In one aspect, in combination with any example method above or below, the determining step includes determining a number of sentient beings present within the field of view and the method further includes associating the environment data with the number of sentient beings.

In one aspect, in combination with any example method above or below, the environmental sensor includes at least one of a carbon dioxide sensor, a volatile organic compounds sensor, and an optical sensor.

In one embodiment presented in this disclosure, a wireless access point system includes an environmental sensor adapted to detect an environmental parameter of an area; and a wireless access point that includes a wireless communication module adapted to provide a wireless communication signal, a radar module adapted to provide, via the wireless communication signal, a radar with a field of view of or within the area, and an object detection module adapted to determine if one or more sentient beings are present within the field of view, the wireless access point system adapted to calibrate the environmental sensor based on the object detection module determining, for a time duration, an absence of the one or more sentient beings.

In one aspect, in combination with any example system above or below, the environmental sensor includes at least one of a carbon dioxide sensor, gas sensor, volatile organic compounds sensor, a camera, an optical sensor, a pressure sensor, a humidity sensor, and an entry sensor. In one aspect, in combination with any example system above or below, the wireless access point includes the carbon dioxide sensor.

In one aspect, in combination with any example system above or below, the wireless communication module is adapted to provide at least a wireless communication channel with a center frequency between 50 GHz and 70 GHz. In one aspect, in combination with any example system above or below, the wireless communication module is adapted to provide a plurality of wireless communication channels with respective center frequencies between 1 GHz and 70 GHz.

In one aspect, in combination with any example system above or below, the object detection module is adapted to determine a number of sentient beings that are present within the field of view.

EXAMPLE EMBODIMENTS

"Video content analysis" (VCA) includes automatically analyzing video to detect and determine temporal and spatial events via one or more algorithms. Example VCA techniques include object detection, face recognition, and alphanumeric recognition of digital images and/or videos. "Object detection" detects, for example, instances of stationary objects, moving objects, and/or sentient beings (e.g., animals and humans) in radar data, digital images, and/or videos. In one aspect, object detection includes sematic segmentation, thereby identifying and/or classifying particular objects such as people, desks, chairs, and robots, among other examples.

In one aspect, the wireless access point fuses radar data and environmental sensor data for a monitored area. For example, a carbon dioxide sensor may be re-calibrated in response to a radar detecting the absence of sentient beings for a predetermined duration, thereby reducing sensor data uncertainly and inaccuracies. In one aspect, environmental sensor data may be a data input for an object detection model that also receives radar data. For example, object detection may occur in response to environmental sensor values passing threshold values, which may generally indicate the presence and/or absence of sentient beings. In one aspect, environmental sensor data is a data input for training an object detection model to identify, among other things, background objects (e.g., furniture; robots) of an area, which may be filtered or otherwise excluded from objection detection processing such as target tracking of sentient beings.

FIG. 1 shows environment monitoring system 100 for room 128. System 100 includes wireless access point 102, also referred to as "access point 102". In one aspect, wireless access point 102 includes environmental sensor(s) 104, antenna array 106, environmental sensor module 108, sensor data module 110, sensor calibration module 112, radar module 114, alert module 116, and object detection module 117. Wireless access point 102 may be operably coupled to environmental sensor(s) 104 that are mounted on or within access point 102 and/or environmental sensor(s) 104 that are discrete, external devices communicatively coupled to access point 102 for providing sensor data and receiving sensor calibration data.

Wireless access point 102 may include or otherwise be operably coupled to user interface 118 and optical sensor(s) 129. For example, optical sensor(s) 129 may be a white-light or infra-red camera that is mounted on or within access point 102 or a discrete device that is communicatively coupled to access point 102 for providing image data 133. Image data 133 may include images, video, and/or object detection data derived therefrom such as semantic labeling (e.g., "person", "chair", "robot") that is provided by VCA and/or object detection techniques.

Display unit 120 may be a display or light feature (e.g., an LED) mounted on or within access point 102 and/or a discrete device that is communicatively coupled to access point 102. Similarly, audio unit 124 may be a speaker that is mounted on or within access point 102 and/or a separate unit that is communicatively coupled to access point 102.

Wireless access point 102, in one aspect, provides a plurality of wireless communication channels for an area such as room 128. A wireless communication channel (e.g., channel 201 of FIG. 2) may have a center frequency between 1 GHz and 70 GHz. In one aspect, wireless communication channel 201 may have a center frequency between 50 GHz and 70 GHz. In one aspect, wireless access point may implement IEEE 802.11ay and/or IEEE 802.11ad wireless communication standards.

In aspect, access point 102, via radar module 114 and antenna array 106, may provide a radar that utilizes wireless communication signals. In one aspect, the antenna array 106 is arranged with radar field of view 107 for detecting sentient beings within area 105, which is monitored by environmental sensor 104.

IEEE 802.11ay and IEEE 802.11ad standards include recommendations for providing a monostatic radar (e.g., an mmWave radar) via access point 102, although alternative or additional aspects include multi-static radar embodiments.

In one aspect, 60 GHz wireless communication channels enable highly accurate counting and/or tracking of people (e.g., sentient beings) in the vicinity of access point 102. For example, communication packets may include Golay complementary sequences with correlation properties that are suitable for radar.

In one aspect, radar module 114 may receive channel estimation fields (CEF) with cycle Golay sequences as an input for a radar algorithm. In one aspect, antenna array 106 includes mmWave (millimeter wave) transceivers to transmit and receive wireless communication signals at or around 60 GHz. In one aspect, access point 102 provides a monostatic radar with the following characteristics:

Angular resolution of 4 degrees with an antenna array of 32 elements (raw)

Range resolution of 9 centimeters (raw at 1.76 Gigasample-Per-Second)

Doppler resolution of a 0.5 a meter per second for 5 millisecond sampling periods Micro-movement differential resolution of 0.1 millimeter (raw)

In one aspect, object detection module 117 tracks or otherwise detects people 130a, 130b, 130c, 130d, and 130e for determining the presence (and/or non-presence) of sentient beings within room 128. In one aspect, radar module 114 and/or object detection module 117 filters fixed and other non-sentient objects from sentient being detection. For example, desks 132a and 132b are generally fixed objects that may partially define a background radar image. Robotic arm 134 and fan 136 are moving objects, but, in some aspects, follow a fixed or other pre-determined path, which can also be filtered from sentient being detection.

In one aspect, image data 133 is obtained from optical sensor 129, which has optical field of view 131 of or within room 128. In one aspect, image data 133 may train an objection detection model, as further detailed in FIG. 5. For example, image-based object detection by module 117 may verify or disprove a determination, based on radar data, of the absence of sentient beings. If a determined absence of sentient beings is verified, however, radar-detected objects such as desks 132a and 132b, robotic arm 134, and fan 136 can be filtered for further determinations, as further detailed in FIG. 5.

In one aspect, alert module 116 may provide or cause to provide visual alert 122 and/or audio alert 126 in response to, for example, elevated $CO_2$ levels. In one aspect, access point 102 includes interface 118, thereby access point 102 may provide alerts 122 and/or 126. Additionally or alternatively, interface 118 may include an external video monitor that includes display unit 120 and audio unit 124 and is operably coupled to access point 102, thereby providing alerts 122 and/or 126 via the external video monitor.

Figure 2:
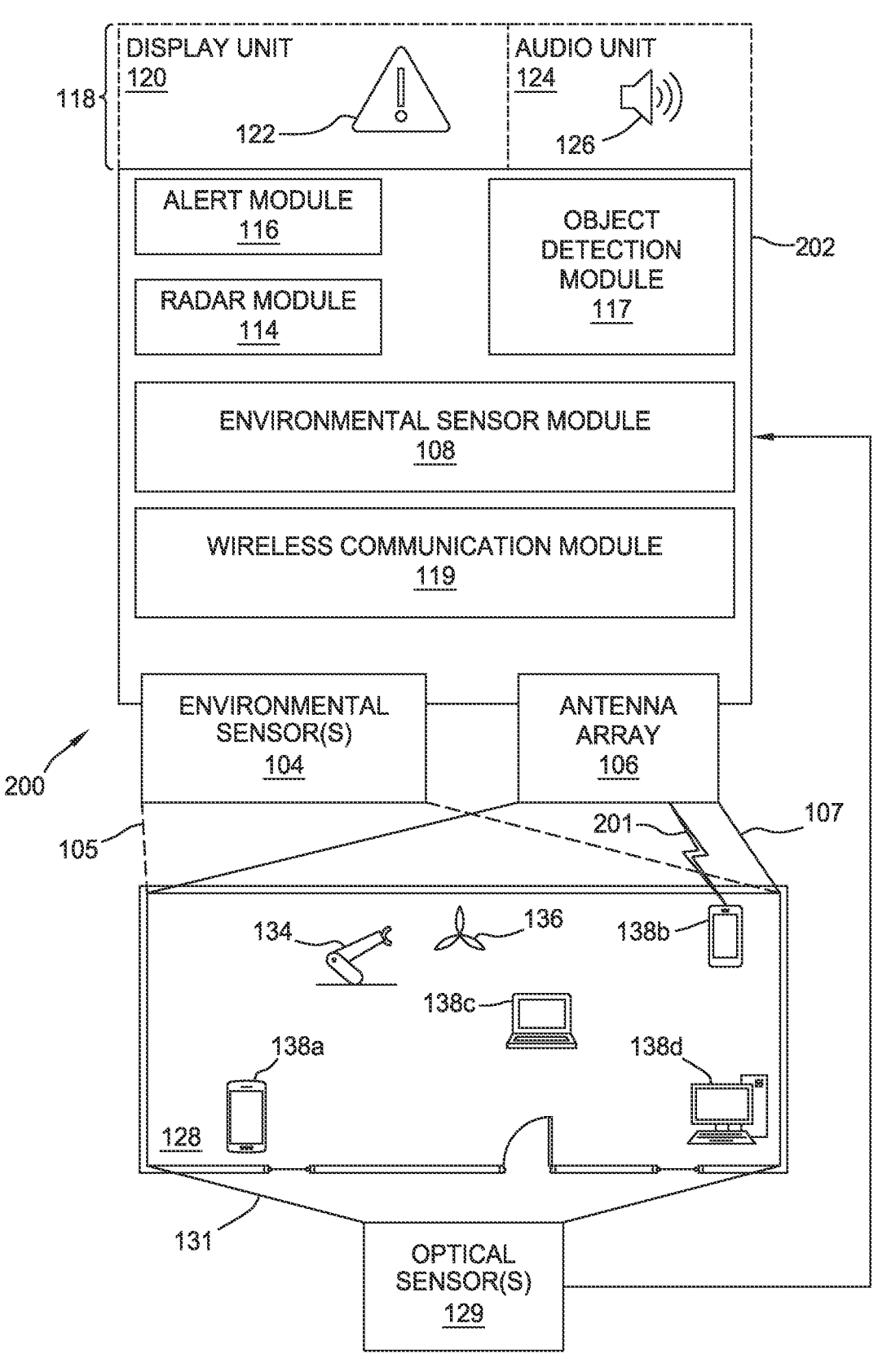
FIG. 2 depicts examples of an environment monitoring system.

Alternatively or additionally, user interface 118 may be an interface of one or more client devices 138a, 138b, 138c, and 138d, as shown in FIG. 2. In such embodiments, alert module 116 of wireless access point 202 may cause one or more of client devices 138a, 138b, 138c, and 138d to provide visual alert 122 and/or audio alert 126.

In one aspect, one or more of client devices 138a, 138b, 138c, and 138d are communicatively coupled to wireless communication module 119 via one or more wireless communication channels such as wireless communication channel 201. In such embodiments, access point 202 of environment monitoring system 200 may verify or disprove a determination of an absence of sentient beings based on a number or type of client devices that are communicatively coupled to access point 202. For example, robotic arm 134, and fan 136 may be client devices of access point 202, which do not necessary indicate the presence of people in contrast to a communicative coupling with client devices 138a, 138b, 138c, and/or 138d. For example, client devices such as smartphones, laptops, and desktop computers may be associated, via a communication channel 201 of access point 202, with a device type, data types (e.g., video streaming; websites), data rate patterns, and/or location change parameters that indicate a person is using and/or moving, for example, client device 138b.

In one aspect, an aggregated client device count of client devices communicatively coupled to 60 GHZ, 6 GHZ, 5 GHZ, and/or 2.4 GHz communication channels of an access point may, for example, be a basis for determining a number of sentient beings, verify a determined number of sentient beings based on radar data, and/or disprove a determination of an absence of sentient beings.

Figure 3:
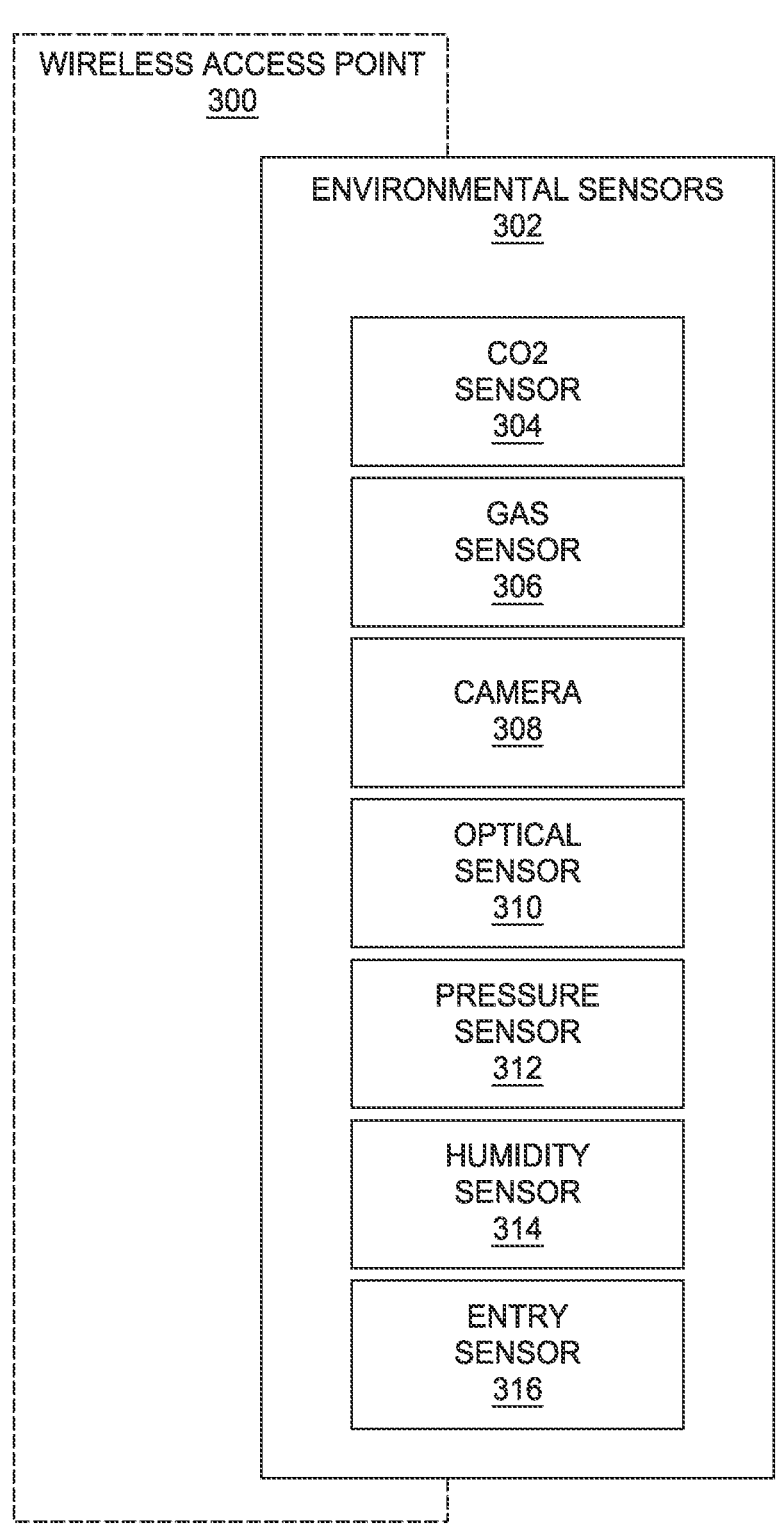
FIG. 3 depicts examples of environmental sensors.

FIG. 3 shows environmental sensors 302, which may be a component of wireless access point 300 and/or an external device that is communicatively coupled to wireless access point 300. In one aspect, environmental sensors 304 may include $CO_2$ sensor 304, gas sensor 306, camera 308, and/or optical sensor 310. $CO_2$ sensor 304 may be a nondispersive infrared (NDIR) carbon sensor, which includes an infrared light source and detector to determine the number of $CO_2$ molecules in the sample gas that is arranged therebetween, thereby measuring $CO_2$ levels of an area. In one aspect, $CO_2$ sensor 304 may be a single channel NDIR sensor.

In one aspect, an area-specific floor value may be accurately determined based on the lowest $CO_2$ readings after installation of $CO_2$ sensor 304 and/or access point 300. An accurate floor value may be determined based on the lowest measurement(s) of $CO_2$ levels across, for example, one or more days. In one aspect, a determined floor value may be transmitted to subsequent access points within, for example, a wireless communicative range of access point 300. Additionally or alternatively, access point 300 may calibrate other $CO_2$ sensors (e.g., gas sensor 306) with a floor value that is based on the sensor data from $CO_2$ sensor 304.

Gas sensor 306 may be a redundant $CO_2$ sensor or other gas sensor such as a Volatile Organic Compounds (VOC) sensor, barometric pressure sensor, ambient temperature sensor, relative humidity sensor or some combinations thereof of a sensor package. In one aspect, data from a redundant $CO_2$ sensor may be compared with data from $CO_2$ sensor 304 for comparing, among other things, relative drift or other inaccuracies of each sensor.

Camera 308 may include a wide-angle lens for obtaining white light, polarized light, and/or infrared light, among other examples. Optical sensor 310 may be a further camera with an overlapping and/or complementary field of view to camera 308. For example, each respective field of view may minimally overlap so to optimize the total field of view between camera 308 and optical sensor 310. Alternatively, each respective field of view may substantially overlap such that each field of view is trained on the same or substantially the same area.

Pressure sensor 312 and humidity sensor 314 may be co-packaged with $CO_2$ sensor 304 and/or gas sensor 306. Pressure sensor 312 may be a barometric pressure sensor and humidity sensor 314 may measure relative humidity of an area. Entry sensor 316 generally detects people entering and exiting a monitored area. Entry sensor 316 may be based on image or video data and/or infrared sensor data, which may control opening and closing of a door. Example entry sensors 316 include cameras and/or infrared motion sensors.

Figure 4:
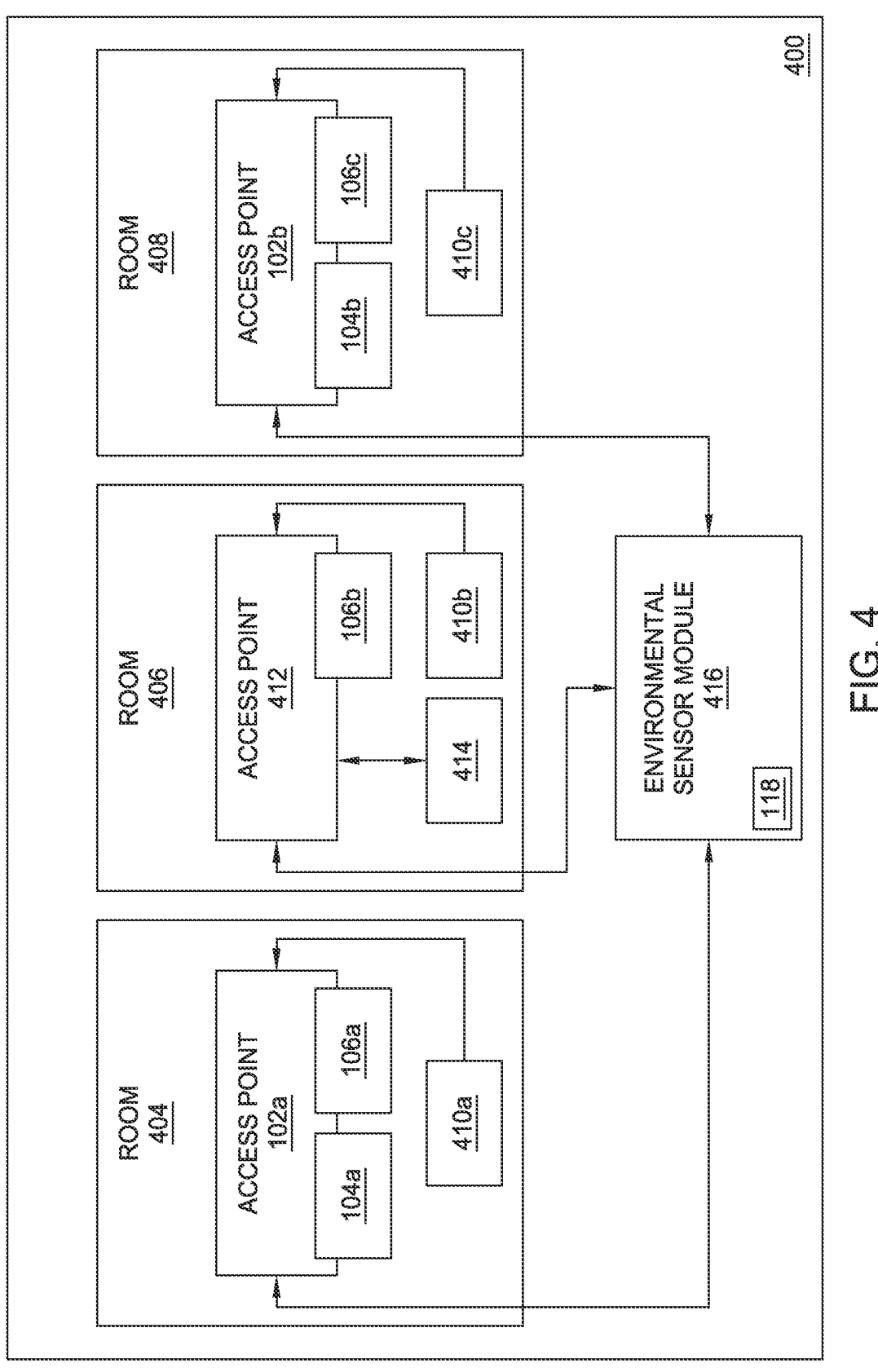
FIG. 4 depicts examples of an environment monitoring system.

FIG. 4 depicts environment monitoring system 400, which includes wireless access points 102a, 412, and 102b that are respectively arranged within rooms 404, 406, and 408. Access points 102a and 102b respectively include environmental sensor(s) 104a and 104b. In contrast, access point 412 is communicatively coupled with external environmental sensor(s) 414. In one aspect, an access point includes internal environmental sensors and is communicatively coupled to external environmental sensors such as camera 410a, 410b, and 410c. Additionally or alternatively, a wireless access point may include a camera.

Wireless access points 102a, 412, and 102b respectively include antenna array 106a, 106b, and 106c. In one aspect, environmental sensor module 416 is operably coupled to access points 102a, 412, and 102b. In one aspect, an environmental sensor module and its functions may occur within an access point, as shown in FIG. 1. Alternatively or additionally, environmental sensor module 416 may be a centralized module that is communicatively coupled with multiple access points, as shown in FIG. 4.

Module 416 may be operably coupled to user interface 118 for providing, among other examples, access-point specific environmental sensor data and alerts.

Figure 5:
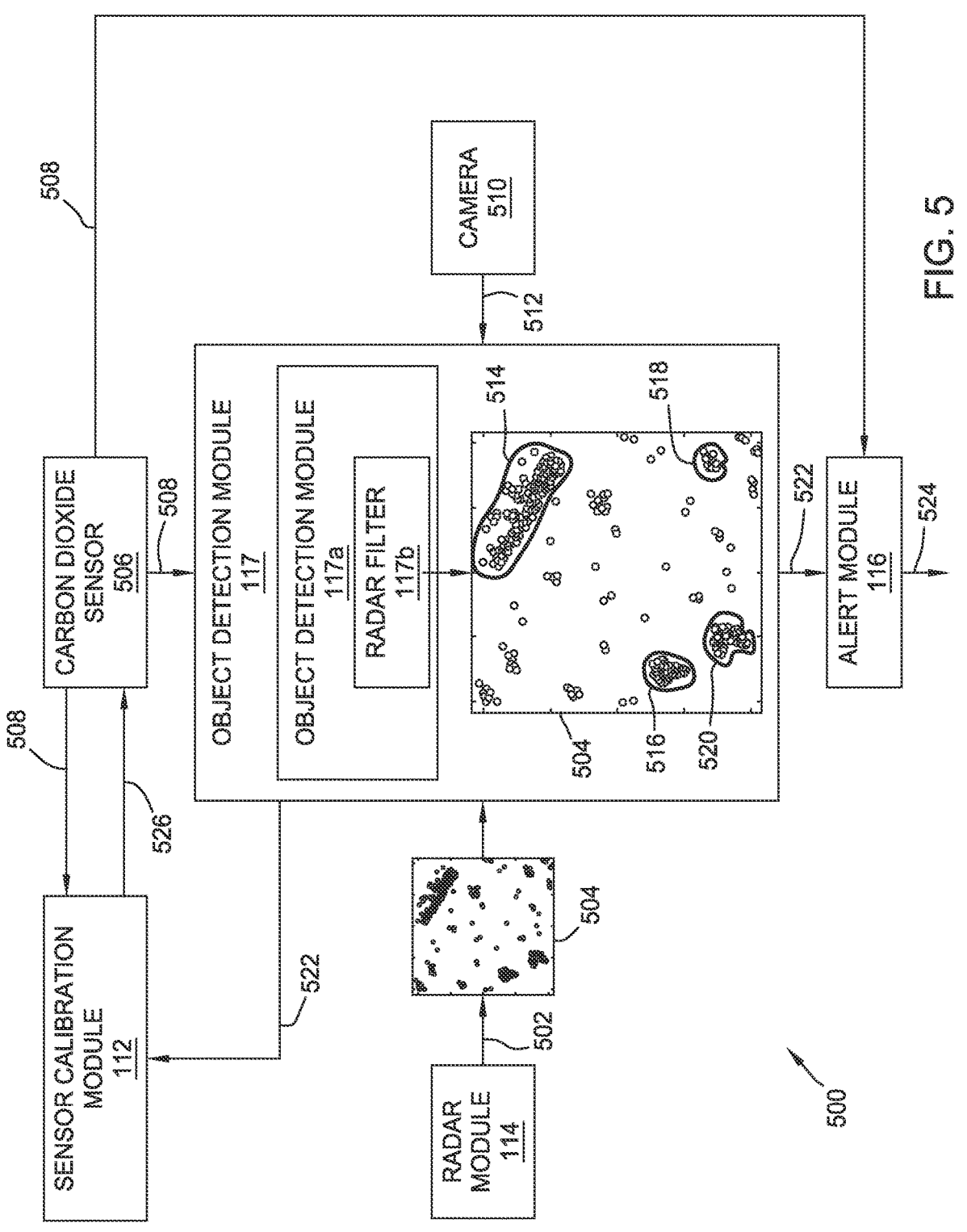
FIG. 5 depicts an example of an environment monitoring system.

FIG. 5 depicts environment monitoring system 500, which may include sensor calibration module 112, radar module 114, alert module 116, object detection module 117, carbon dioxide sensor 506, and camera 510.

In one aspect radar module 114 may perform object detection based on radar measurements for determining target echoes. In one aspect target echoes are based on a detection threshold determined by a false alarm rate and detection probability. Target resolution involves the resolving of closely spaced objects and cluster into individual object through techniques such as Doppler processing for velocity resolution or pulse compression for range resolution.

Target-to-track association assigns individual target measurements to potential tracks. Target track filtering estimates an object's position, velocity, and acceleration based on radar measurements. Target track filtering minimizes the error between the object's predicted and actual position, velocity, and/or acceleration.

In one aspect, radar module 114 provides target echo data 502, including radar point cloud 504, to objection detection module 117, which may include object detection model 117a and radar filter 117b. Object detection model 117a may segment point cloud 504 into clusters 514, 516, 518, and 520. In one aspect, clusters 514, 516, 518, and 520 may define a baseline cluster arrangement, which is indicative of an absence of the sentient beings. For example, clusters 514, 516, 518, and 520 may represent static or other non-sentient objects like robots.

In one aspect, radar filter 117b may filter or otherwise exclude one or more clusters 514, 516, 518, and 520 from sentient being detection, target track calculations, and/or other radar data processing techniques. In one aspect, radar filter 117b may filter sentient being identifications and/or classifications based on environmental sensor data such as $CO_2$ data 508 from carbon dioxide sensor 506 and image data 512 from camera 510. For example, $CO_2$ data 508 and/or image data 512 may indicate and/or verify the absence of people. Radar filter 117b may thereby identify an erroneous detection of a sentient being by object detection model 117a and filter said detection from further data processing.

In one aspect, object detection module 117 may provide object detection data 522 to sensor calibration module 112 and alert module 116. In one aspect, object detection data 522 may provide a determined number of sentient beings within a radar's field of view.

In one aspect, sensor calibration module 112 may provide calibration data 526 to carbon dioxide sensor 506 based on the object detection data 522. For example, sensor calibration module 112 may provide calibration data 526 in response to the object detection data 522 indicating, for a time duration, an absence of sentient beings within the field of view of the radar. In one aspect, sensor calibration module 112 may calibrate carbon dioxide sensor 506 to a floor value after an hour or longer period of consecutive determinations of the absence of sentient beings. In one aspect, the floor value may be calculated after access point installation as previously described. Alternatively, the floor value may be a predetermined value such as 400 parts per million (ppm).

In one aspect, alert module 116 provides alert data 524 based on object detection data 522 and $CO_2$ data 508. For example, alert module 116 may provide alert data 524 in response to $CO_2$ data 508 having a $CO_2$ level (e.g., a sensor reading) above a threshold. In one aspect, the $CO_2$ level threshold may increase based on the number of detected sentient beings within a room or other area. In one aspect, alert data 524 indicates an anomaly such as a fire, gas leak, and/or sensor error or other indication that a sensor needs replacement.

As described above, in one aspect, environment monitoring system 500 fuses disparate sensor data in training object detection model 117 and/or generating alerts by alert module 116, thereby minimizing errors and uncertainty inherent in individual sensor data.

Figure 6:
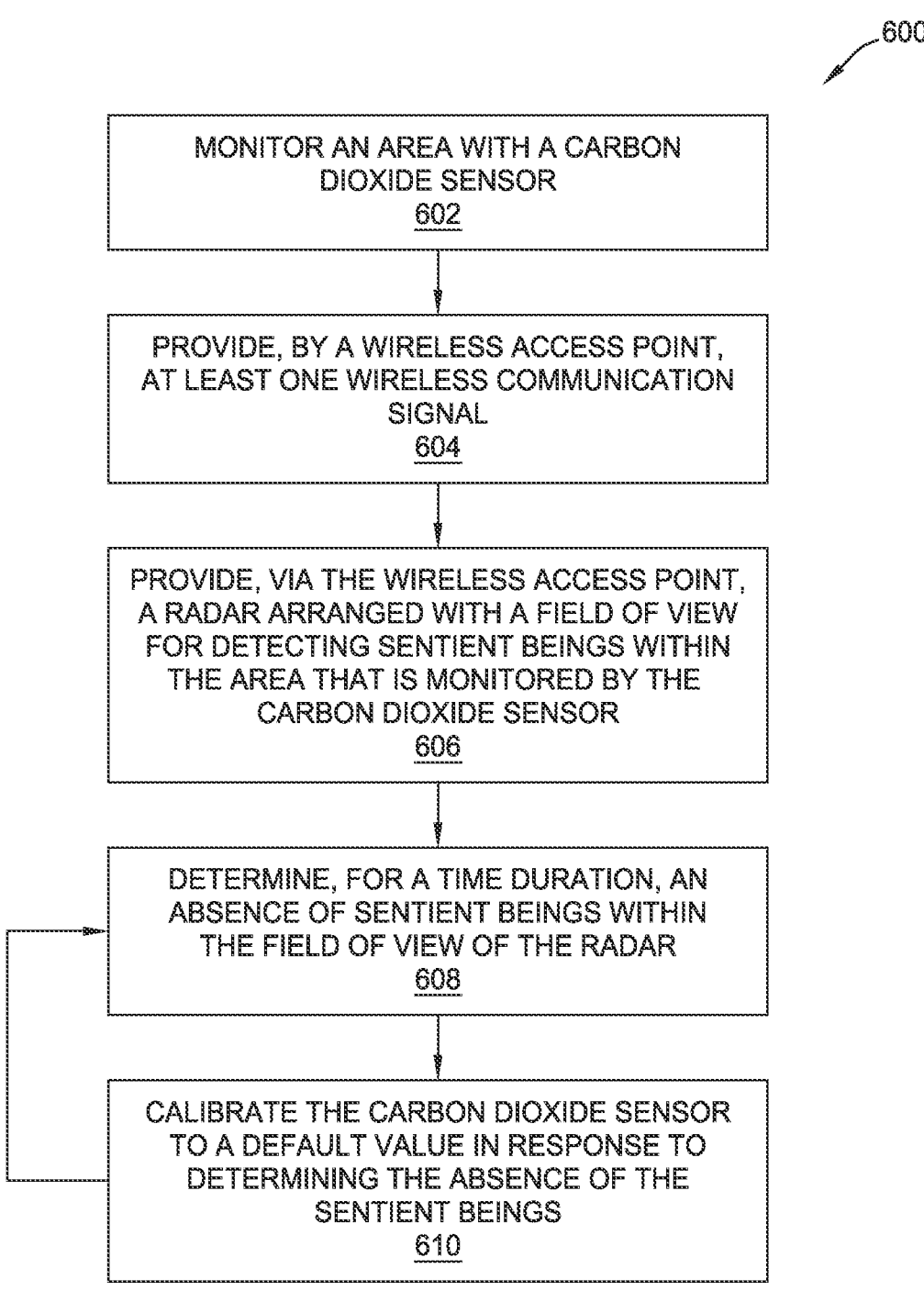
FIG. 6 depicts an example of an environment monitoring method.

FIG. 6 depicts environment monitoring method 600. At block 602, a carbon dioxide sensor monitors an area for $CO_2$ levels. At block 604, a wireless access point provides at least one wireless communication signal. In one aspect, a wireless communication channel (of the wireless communication signal) has a center frequency between 50 GHz and 70 GHz. In one aspect, the wireless access point may provide a plurality of wireless communication signals with a plurality of wireless communication channels with respective center frequencies between 1 GHz and 70 GHz.

At block 606, the wireless access point provides a radar that is arranged with a field of view for detecting sentient beings that are generally within the area being monitored by the carbon dioxide sensor. In one aspect, the wireless access point provides a radar based at least on one wireless communication signal. In one aspect, the wireless access point provides a radar based on a wireless communication channel (of the wireless communication signal) that has a center frequency between 50 GHz and 70 GHz. In one aspect, communication packets of the wireless communication channel may include Golay complementary sequences with correlation properties that are suitable for radar. For example, in one aspect, the wireless access point may receive channel estimation fields (CEF) with cycle Golay sequences as an input for a radar algorithm In one aspect, the wireless access point fuses radar data and environmental sensor data for a monitored area. In one aspect, environmental sensors data may be a data input for an object detection model that also receives radar data.

At block 608, the wireless access point may determine, for a time duration, an absence of sentient beings within the field of view of the radar. If the determination of block 608 is affirmative, a wireless access point may, at block 610, calibrate the carbon dioxide sensor to a default value in response to determining the absence of the sentient beings. In one aspect, the default value may be a pre-determined floor value such as 400 ppm. In one aspect, the default value may be determined by the access point based on a lowest band of measured carbon dioxide levels from a carbon dioxide sensor. In one aspect, a floor value is determined based on carbon dioxide levels that are measured after and/or in response to block 608. Method 600 may then return to block 608 for further calibrations and/or floor value calculations.

FIG. 7 depicts environment monitoring method 700. At block 702, a wireless access point provides a radar with a field of view for detecting sentient beings within an area. At block 704, an environmental sensor generates environment data indicating a presence of sentient beings within the area. For example, raising measured carbon dioxide levels may be indicative of the presence of people. Block 706 includes determining, by the object detection module, if sentient beings are present within the radar's field of view. In one aspect, the determination of block 706 may be in response to block 704, thereby selectively engaging block 706.

FIG. 8 depicts environment monitoring method 800, which includes blocks for determining block 706. At block 706a, the object detection module tracks detected objects arranged within the field of view. In one aspect, the object detection module is a module of the wireless access point. At block 706b, the detected objects may be filtered based on at least the environment data such that the object detection module excludes non-sentient detected objects. In one aspect, filtering block 706b may include determining, by the object detection module, a baseline cluster arrangement based at least on the environment data, the baseline cluster arrangement indicating an absence of the sentient beings.

FIG. 9 depicts environment monitoring method 900. At block 902, a wireless access point determines a number of client devices that are operably coupled to the wireless access point via a wireless communication channel. In one aspect, an aggregated client device count is determined based on a number of client devices that are communicatively coupled to 60 GHz, 6 GHZ, 5 GHZ, and/or 2.4 GHz communication channels that are provided by the wireless access point.

At block 904, the wireless access point may determine a number of sentient beings that are present within the field of view based at least on the number of client devices that are operably coupled to the wireless access point. For example, in one aspect, the number of communicatively coupled devices may be compared and/or averaged with a determined number of sentient beings based on radar data. In one aspect, the determined number of sentient beings is the greater or lesser of the cumulative number of communicatively coupled devices and the determined number of sentient beings based on radar data.

At block 906, a wireless access point may associate the environment data with the determined number of sentient beings. In one aspect, a range of $CO_2$ levels may be associated with a respective number of sentient beings. In one aspect, anomalies such as inaccurate measurements from defective sensors, fires, and/or overcrowded rooms may trigger an alert based on $CO_2$ levels that fall outside the range of $CO_2$ levels associated with a determined number of sentient beings.

In the current disclosure, reference is made to various embodiments. However, the scope of the present disclosure is not limited to specific described embodiments. Instead, any combination of the described features and elements, whether related to different embodiments or not, is contemplated to implement and practice contemplated embodiments. Additionally, when elements of the embodiments are described in the form of "at least one of A and B," or "at least one of A or B," it will be understood that embodiments including element A exclusively, including element B exclusively, and including element A and B are each contemplated. Furthermore, although some embodiments disclosed herein may achieve advantages over other possible solutions or over the prior art, whether or not a particular advantage is achieved by a given embodiment is not limiting of the scope of the present disclosure. Thus, the aspects, features, embodiments and advantages disclosed herein are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, the embodiments disclosed herein may be embodied as a system, method or computer program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a computer program product embodied in one or more computer readable medium(s) having computer readable program code embodied thereon.

Program code embodied on a computer readable medium may be transmitted using any appropriate medium, including but not limited to wireless, wireline, optical fiber cable, RF, etc., or any suitable combination of the foregoing.

Computer program code for carrying out operations for embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatuses (systems), and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block(s) of the flowchart illustrations and/or block diagrams.

These computer program instructions may also be stored in a computer readable medium that can direct a computer, other programmable data processing apparatus, or other device to function in a particular manner, such that the instructions stored in the computer readable medium produce an article of manufacture including instructions which implement the function/act specified in the block(s) of the flowchart illustrations and/or block diagrams.

The computer program instructions may also be loaded onto a computer, other programmable data processing apparatus, or other device to cause a series of operational steps to be performed on the computer, other programmable apparatus or other device to produce a computer implemented process such that the instructions which execute on the computer, other programmable data processing apparatus, or other device provide processes for implementing the functions/acts specified in the block(s) of the flowchart illustrations and/or block diagrams.

The flowchart illustrations and block diagrams in the Figures illustrate the architecture, functionality, and operation of possible implementations of systems, methods, and computer program products according to various embodiments. In this regard, each block in the flowchart illustrations or block diagrams may represent a module, segment, or portion of code, which comprises one or more executable instructions for implementing the specified logical function (s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

In view of the foregoing, the scope of the present disclosure is determined by the claims that follow.

We claim:

1. A method comprising:
   providing a radar using a wireless communication signal of a wireless access point, the radar arranged with a field of view for detecting sentient beings within an area that is monitored by a carbon dioxide sensor;
   determining, for a time duration, a number of sentient beings within the field of view of the radar, comprising:
      segmenting a radar point cloud, representing objects detected within the field of view of the radar, into a plurality of clusters based on spatial proximity of the detected objects,
      identifying one or more clusters, from the plurality of clusters, as non-sentient clusters based on environmental sensor data,
      excluding the identified non-sentient clusters from the plurality of clusters, and
      verifying, based on the environmental sensor data and a number of client devices coupled to the wireless access point, one or more remaining clusters, from the plurality of clusters, to determine the number of sentient beings present within the field of view;

defining a carbon dioxide threshold value based on the number of sentient beings present within the field of view; and
   generating an alert in response to carbon dioxide data, detected by the carbon dioxide sensor, exceeding the carbon dioxide threshold value.

2. The method of claim 1, wherein the wireless access point is operably coupled to the carbon dioxide sensor.

3. The method of claim 2, wherein the wireless access point comprises the carbon dioxide sensor.

4. The method of claim 1, further comprising providing, by the wireless communication signal, a wireless communication channel with a center frequency between 50 GHz and 70 GHz.

5. The method of claim 1, further comprising providing, by the wireless access point, a plurality of wireless communication channels with respective center frequencies between 1 GHz and 70 GHz.

6. The method of claim 1, further comprising:
   determining, by the wireless access point, an absence of sentient beings within the field of view of the radar in response to determining that the number of sentient beings is zero; and
   calibrating, by the wireless access point, the carbon dioxide sensor to a default value in response to determining the absence of the sentient beings.

7. The method of claim 6, further comprising determining, based on carbon dioxide sensor data, a floor value as the default value.

8. A method for operating a radar system, the radar system comprising a wireless access point, an object detection module, and an environmental sensor, the method comprising:
   providing, using the wireless access point, a radar with a field of view for detecting sentient beings within an area that is monitored by the environmental sensor;
   generating, by the environmental sensor, environmental sensor data indicating a presence of one or more of the sentient beings within the area; and
   determining, by the object detection module, if the sentient beings are present within the field of view, the determining step comprising:
      segmenting a radar point cloud, representing objects detected within the field of view of the radar, into a plurality of clusters based on spatial proximity of the detected objects,
      identifying one or more clusters, from the plurality of clusters, as non-sentient clusters based on the environmental sensor data,
      excluding the identified non-sentient clusters from the plurality of clusters, and
      verifying, based on the environmental sensor data and a number of client devices coupled to the wireless access point, one or more remaining clusters, from the plurality of clusters, to determine a number of sentient beings present within the field of view;
   defining a carbon dioxide threshold value based on the number of sentient beings present within the field of view; and
   generating an alert in response to carbon dioxide data, among the environmental sensor data, exceeding the carbon dioxide threshold value.

9. The method of claim 8, wherein the environmental sensor comprises a carbon dioxide sensor, and the wireless access point is operably coupled to the carbon dioxide sensor.

10. The method of claim 8, further comprising providing, by a wireless communication signal of the wireless access point, a wireless communication channel with a center frequency between 50 GHz and 70 GHz.

11. The method of claim 8, wherein the determining step comprises determining, by the object detection module, a baseline cluster arrangement based at least on the environmental sensor data, the baseline cluster arrangement indicating an absence of the sentient beings.

12. The method of claim 8, wherein the environmental sensor comprises at least one of a carbon dioxide sensor, a volatile organic compounds sensor, and an optical sensor.

13. A wireless access point system comprising:

an environmental sensor adapted to detect an environmental parameter of an area; and a wireless access point comprising:

a wireless communication module adapted to provide a wireless communication signal;

a radar module adapted to provide, via the wireless communication signal, a radar with a field of view of or within the area; and an object detection module adapted to determine if one or more sentient beings are present within the field of view, wherein determining, for a time duration, a number of the one or more sentient beings within the field of view comprises:

segmenting a radar point cloud, representing objects detected within the field of view of the radar, into a plurality of clusters based on spatial proximity of the detected objects, identifying one or more clusters, from the plurality of clusters, as non-sentient clusters based on environmental sensor data, excluding the identified non-sentient clusters from the plurality of clusters, and verifying, based on the environmental sensor data and a number of client devices coupled to the wireless access point, one or more remaining clusters, from the plurality of clusters, to determine the number of the one or more sentient beings present within the field of view; and an alert module adapted to define a carbon dioxide threshold value based on the number of the one or more sentient beings present within the field of view and to generate an alert in response to carbon dioxide data, among the environmental sensor data, exceeding the carbon dioxide threshold value.

14. The wireless access point system of claim 13, wherein the environmental sensor comprises at least one of a carbon dioxide sensor, gas sensor, volatile organic compounds sensor, a camera, an optical sensor, a pressure sensor, a humidity sensor, and an entry sensor.

15. The wireless access point system of claim 14, wherein the wireless access point comprises the carbon dioxide sensor.

16. The wireless access point system of claim 13, wherein the wireless communication module is adapted to provide at least a wireless communication channel with a center frequency between 50 GHz and 70 GHz.

17. The wireless access point system of claim 13, wherein the wireless communication module is adapted to provide a plurality of wireless communication channels with respective center frequencies between 1 GHz and 70 GHz.

* * * * *